United States Patent
Kim

(10) Patent No.: US 10,961,938 B2
(45) Date of Patent: Mar. 30, 2021

(54) DIAGNOSIS METHOD FOR ETHANOL SENSOR OF FFV AND FFV OPERATED THEREBY

(71) Applicant: Hyundai Kefico Corporation, Gunpo-si (KR)

(72) Inventor: Young Jin Kim, Seoul (KR)

(73) Assignee: Hyundai Kefico Corporation, Gunpo-si (KR)

( * ) Notice: Subject to any disclaimer, the term of this patent is extended or adjusted under 35 U.S.C. 154(b) by 0 days.

(21) Appl. No.: 16/662,791

(22) Filed: Oct. 24, 2019

(65) Prior Publication Data

US 2020/0132010 A1     Apr. 30, 2020

(51) Int. Cl.
*F02D 41/22* (2006.01)
*F02D 19/06* (2006.01)
(Continued)

(52) U.S. Cl.
CPC ............ *F02D 41/222* (2013.01); *B60K 15/03* (2013.01); *F02D 19/0623* (2013.01); *F02D 19/0634* (2013.01); *F02D 19/0652* (2013.01); *F02D 19/0655* (2013.01); *F02D 19/081* (2013.01); *F02D 19/084* (2013.01); *F02D 19/087* (2013.01); *F02D 41/3005* (2013.01); (Continued)

(58) Field of Classification Search
CPC .. F02D 41/222; F02D 41/3005; F02D 19/088; F02D 19/087; F02D 19/082; F02D 19/081; F02D 19/0623; F02D 19/0634; F02D 19/084; F02D 19/0626; F02D 19/0652; B60K 15/03; G01N 33/2852
See application file for complete search history.

(56) References Cited

U.S. PATENT DOCUMENTS

| 2009/0024304 A1* | 1/2009 | Takubo | F02D 41/2461 701/103 |
| 2009/0306875 A1* | 12/2009 | Jiang | F02D 41/2451 701/102 |

(Continued)

FOREIGN PATENT DOCUMENTS

| JP | 2009-036107 A | 2/2009 |
| JP | 2010-048117 A | 3/2010 |

(Continued)

*Primary Examiner* — George C Jin
(74) *Attorney, Agent, or Firm* — Morgan, Lewis & Bockius LLP

(57) ABSTRACT

The present invention relates to a diagnosis method for an ethanol sensor of a flexible fuel vehicle, the diagnosis method including: a) the fuel refilling detection step of detecting whether fuel is filled to a fuel tank; b) the maximum changeable content range calculation step of calculating a content range of ethanol in the fuel stored in the fuel tank; c) the ethanol sensor value acquirement step of determining whether the data detected from an ethanol sensor converges into a given value; d) the oxygen sensor value acquirement step of determining whether the data detected from an oxygen sensor converges into a given value; and e) the ethanol sensor abnormality determination step of determining that an error is generated from the ethanol sensor if the data acquired at the ethanol sensor value acquirement step or the data acquired at the step is not a value in the calculated range.

15 Claims, 5 Drawing Sheets

(51) Int. Cl.
  *B60K 15/03*  (2006.01)
  *F02D 41/30*  (2006.01)
  *G01N 33/28*  (2006.01)
  *F02D 19/08*  (2006.01)

(52) U.S. Cl.
  CPC .......... *G01N 33/2852* (2013.01); *B60K 2015/03217* (2013.01); *B60K 2015/03355* (2013.01); *F02D 2041/224* (2013.01); *F02D 2200/0611* (2013.01); *F02D 2200/0614* (2013.01); *F02D 2200/101* (2013.01)

(56) References Cited

U.S. PATENT DOCUMENTS

| | | | |
|---|---|---|---|
| 2009/0306879 A1* | 12/2009 | Takubo | F02D 41/2461 701/104 |
| 2010/0168984 A1* | 7/2010 | Fournel | F02D 41/0025 701/103 |
| 2011/0208409 A1* | 8/2011 | Snyder | F02D 19/084 701/109 |
| 2012/0047992 A1* | 3/2012 | Sasai | F02D 19/087 73/23.32 |
| 2012/0226425 A1* | 9/2012 | Lunati | G01N 21/359 701/102 |
| 2012/0227707 A1* | 9/2012 | Sasai | F02D 19/084 123/464 |
| 2013/0151120 A1* | 6/2013 | Kim | F02D 41/1498 701/104 |
| 2013/0263824 A1* | 10/2013 | Wakao | F02D 45/00 123/445 |
| 2013/0268209 A1* | 10/2013 | Tashima | G01M 15/04 702/25 |
| 2015/0323481 A1* | 11/2015 | Vanvelzen | F02D 19/087 73/23.32 |
| 2020/0263616 A1* | 8/2020 | Kashid | F02D 19/084 |

FOREIGN PATENT DOCUMENTS

| | | |
|---|---|---|
| JP | 2011-089457 A | 5/2011 |
| JP | 2011-179474 A | 9/2011 |
| JP | 4998742 B2 | 8/2012 |
| JP | 2012-225191 A | 11/2012 |
| JP | 5429407 B2 | 2/2014 |
| JP | 2016-186275 A | 10/2016 |
| KR | 10-0812423 B1 | 3/2008 |
| KR | 10-0980887 B1 | 9/2010 |
| KR | 10-2013-0060565 A | 6/2013 |

* cited by examiner

DIAGNOSIS METHOD FOR ETHANOL SENSOR OF FFV AND FFV OPERATED THEREBY

CROSS REFERENCE TO RELATED APPLICATION OF THE INVENTION

The present application claims the benefit of Korean Patent Application No. 10-2018-0129180 filed in the Korean Intellectual Property Office on Oct. 26, 2018, the entire contents of which are incorporated herein by reference.

BACKGROUND OF THE INVENTION

Field of the Invention

The present invention relates to a diagnosis method for an ethanol sensor of a flexible fuel vehicle (hereinafter, referred to as FFV) and an FFV operated thereby, and more particularly, to a diagnosis method for an ethanol sensor of an FFV and an FFV operated thereby that are capable of accurately recognizing an ethanol content in fuel stored in a fuel tank to reliably determine whether the ethanol sensor is normal.

Background of the Related Art

As environmental pollution is accelerated, recently, environmental regulations in many countries become strictly implemented, and as a result, development of environment-friendly vehicles and supply of alternative fuel have been widely suggested. In Brazil and North America, especially, a plan for supplying bioethanol as alternative fuel has been executed to achieve reduction in an amount of petroleum used and agriculture promotion. In 2017, recently, America allows gasoline containing up to 15% ethanol to be sold, and Brazil has more than 80% FFVs in the entire vehicles.

The bioethanol, which is evaluated as new renewable energy, can decrease production of harmful materials from exhaust gas and can have a small amount of carbon emitted to thus suppress ozone depletion. Further, the bioethanol extracted from plant leaves is neutral in a total amount of carbon emitted through carbon dioxide assimilation and is produced through cultivation to advantageously achieve continuity in production thereof.

In case of the FFV in a conventional practice, it is possible that gasoline-ethanol blended fuel is burned in one engine. At the time, it is very important to recognize an accurate ethanol content in the fuel due to differences in main features, such as air-fuel ratio (gasoline air-fuel ratio of 14.7 and ethanol air-fuel ratio of 9), octane number (gasoline octane number of 92 and ethanol octane number of 111), and so on.

If it is recognized that the ethanol content is less than the real ethanol content, spark advance, which may be possibly performed in ethanol, is not sufficiently utilized, thereby causing inefficiency, and contrarily, if it is recognized that the ethanol content is greater than the real ethanol content, spark advance is excessively performed to generate knocking and preignition, thereby causing an engine to be damaged.

In case of the FFV in the conventional practice, an ethanol content is learned by using an oxygen sensor feedback value on the basis of a difference between air-fuel ratios of gasoline and ethanol. In this case, advantageously, no separate parts are required, unlike a gasoline system, but some problems occur. For example, such problem include long time consumed for learning the ethanol content, generation of noise from the oxygen sensor, aging of the oxygen sensor, and existence in an engine operating range where learning is impossible.

In case of a high efficiency engine having a high combustion pressure like a turbo GDI (Gasoline Direct Injection) engine, it is very important to immediately learn an accurate ethanol content, and accordingly, an ethanol sensor capable of directly measuring the ethanol content in the fuel is increasingly used.

So as to solve the above-mentioned problems, as shown in FIG. 1, a conventional method includes the steps of determining whether an ethanol content learned through an ethanol content learning logic is in a normal range or erroneously learned and, if it is determined that the ethanol content is erroneously learned, changing the ethanol content into an alternative value.

However, the conventional method as shown in FIG. 1 does not solve the problems occurring in the conventional practices perfectly.

Therefore, there is a definite need for the development of a new method capable of solving the problems occurring in the conventional practices.

SUMMARY OF THE INVENTION

Accordingly, the present invention has been made in view of the above-mentioned problems occurring in the related art, and it is an object of the present invention to provide a diagnosis method for an ethanol sensor of an FFV and an FFV operated thereby that are capable of accurately recognizing an ethanol content in the fuel stored in a fuel tank to reliably determine whether the ethanol sensor mounted on a fuel line of the FFV is normal.

To accomplish the above-mentioned object, according to one aspect of the present invention, there is provided a diagnosis method for an ethanol sensor of a flexible fuel vehicle, the flexible fuel vehicle having a fuel refilling detection device disposed in a fuel tank, an ethanol sensor disposed on a fuel supply line, and an oxygen sensor disposed on an exhaust gas emission line, the diagnosis method including: a) the fuel refilling detection step of detecting whether fuel is filled to the fuel tank through the fuel refilling detection device disposed in the fuel tank; b) the maximum changeable content range calculation step of calculating a content range of ethanol in the fuel stored in the fuel tank on the basis of whether the fuel refilled is pure gasoline or pure ethanol; c) the ethanol sensor value acquirement step of calculating an amount of ethanol remaining on a line between the fuel tank and the ethanol sensor, calculating time during which the fuel refilled reaches the ethanol sensor, and after the calculated time is elapsed, determining whether the data detected from the ethanol sensor converges into a given value; d) the oxygen sensor value acquirement step of calculating an amount of exhaust gas remaining on a line between an engine and the oxygen sensor, calculating time during which the exhaust gas of the fuel refilled reaches the oxygen sensor, and after the calculated time is elapsed, determining whether the data detected from the oxygen sensor converges into a given value; and e) the ethanol sensor abnormality determination step of determining that an error is generated from the ethanol sensor if the data acquired at the ethanol sensor value acquirement step or the data acquired at the oxygen sensor value acquirement step is not a value in the calculated range.

According to the present invention, desirably, the fuel refilling detection device disposed in the fuel tank is a fuel level sensor, a fuel refilling switch, or a fuel refilling sensor.

According to the present invention, desirably, the maximum changeable content range calculation step calculates the content range of ethanol in the fuel stored in the fuel tank on the basis of ethanol content data stored in advance before refilling, volume data of the fuel stored in the fuel tank before refilling, and a volume of fuel refilled.

According to the present invention, desirably, the maximum changeable content range calculation step calculates a minimum limit value in a changeable content under the assumption where the fuel refilled is pure gasoline and calculates a maximum limit value in a changeable content under the assumption where the fuel refilled is pure ethanol.

According to the present invention, desirably, the calculated time at the ethanol sensor value acquirement step is acquired by calculating a target value of the fuel remaining between the fuel tank and the ethanol sensor by using length and inner diameter data on the line disposed between the fuel tank and the ethanol sensor, estimating an amount of fuel injected into an interior of the engine, comparing whether the estimated amount of fuel is greater than the target value of the fuel, and calculating the time during which the fuel refilled reaches the ethanol sensor.

According to the present invention, desirably, at the ethanol sensor value acquirement step, if the data detected from the ethanol sensor does not converge into the given value after the calculated time is elapsed, the data is repeatedly detected from the ethanol sensor until the data converges into the given value.

According to the present invention, desirably, at the oxygen sensor value acquirement step, the time during which the exhaust gas of the fuel refilled reaches the oxygen sensor is acquired by calculating time during which the exhaust gas of the fuel reaches the oxygen gas from the engine according to operating ranges, if the data detected from the ethanol sensor converges into the given value, and by calculating change time of fuel from the ethanol sensor to the engine.

According to the present invention, desirably, at the oxygen sensor value acquirement step, the time during which the exhaust gas of the fuel refilled reaches the oxygen sensor is acquired by calculating a remaining amount value of exhaust gas between the fuel tank and the ethanol sensor by using length and inner diameter data on the line disposed between the engine and the oxygen sensor, detecting an emission amount value of exhaust gas per hour from the engine, dividing the remaining amount value of exhaust gas by the emission amount value of exhaust gas per hour, and calculating the time during which the exhaust gas emitted by the combustion of the fuel refilled reaches the oxygen sensor from the engine.

According to the present invention, desirably, the diagnosis method further includes the diagnosis condition determination step of determining whether current operating conditions of the flexible fuel vehicle are under diagnosis conditions after the calculated time is elapsed.

According to the present invention, desirably, at the oxygen sensor value acquirement step, if the data detected from the oxygen sensor does not converge into the given value after the calculated time is elapsed, the data is repeatedly detected from the oxygen sensor until the data converges into the given value.

According to the present invention, desirably, the diagnosis method further includes the lambda control value convergence determination step of determining whether convergence of a deviation or lambda control value from a lambda, 1 of the oxygen sensor is carried out if the data detected from the oxygen sensor converges into the given value.

According to the present invention, desirably, the diagnosis method further includes the lambda control value allowable range determination step of determining whether the lambda control value is within a predetermined target lambda control value allowable range if it determined that convergence of the lambda control value is carried out at the lambda control value convergence determination step.

According to the present invention, desirably, if it is determined that the lambda control value is within the predetermined target lambda control value allowable range at the lambda control value allowable range determination step, it is determined that the ethanol sensor is normal.

According to the present invention, desirably, the diagnosis conditions include constant engine RPM and range condition satisfaction, constant engine load and range condition satisfaction, rich/lean control condition of air-fuel ratio, excessive injection control section, canister purge valve closing, an amount of ethanol evaporated below a given level, error of an air flow measuring system (MAP, HFM), error of an injector, and misfire or knocking error.

To accomplish the above-mentioned object, according to another aspect of the present invention, there is provided a flexible fuel vehicle operated by the diagnosis method for the ethanol sensor according to one aspect of the present invention, the flexible fuel vehicle including: the fuel refilling detection device disposed in the fuel tank to detect whether the fuel is filled to the fuel tank; the ethanol sensor mounted on the fuel supply line between the fuel tank and the engine to detect data on an ethanol content in the fuel supplied from the fuel tank to the engine; the oxygen sensor mounted on the exhaust gas emission line of the exhaust gas discharged from the engine to detect data on an amount of exhaust gas discharged from the engine; and an engine control unit for determining that an error is generated from the ethanol sensor if the data acquired at the ethanol sensor value acquirement step or the data acquired at the oxygen sensor value acquirement step is not a value in the calculated range.

BRIEF DESCRIPTION OF THE DRAWINGS

The above and other objects, features and advantages of the present invention will be apparent from the following detailed description of the embodiments of the invention in conjunction with the accompanying drawings, in which.

DETAILED DESCRIPTION OF THE EMBODIMENTS

Hereinafter, the present invention is disclosed with reference to the attached drawings. Before the description of the present invention, special terms in the description and claims of the present invention are used not to limit the present invention and the scope of the present invention as defined in claims, but just to explain the present invention.

In the description, when it is said that one member is located "above" or "under" another member, it means that one member may come into contact with another member as well as yet another member may exist between the two members. In the description, when it is said that one portion is described as "includes" any component, one element further may include other components unless no specific description is suggested.

Figure 1:
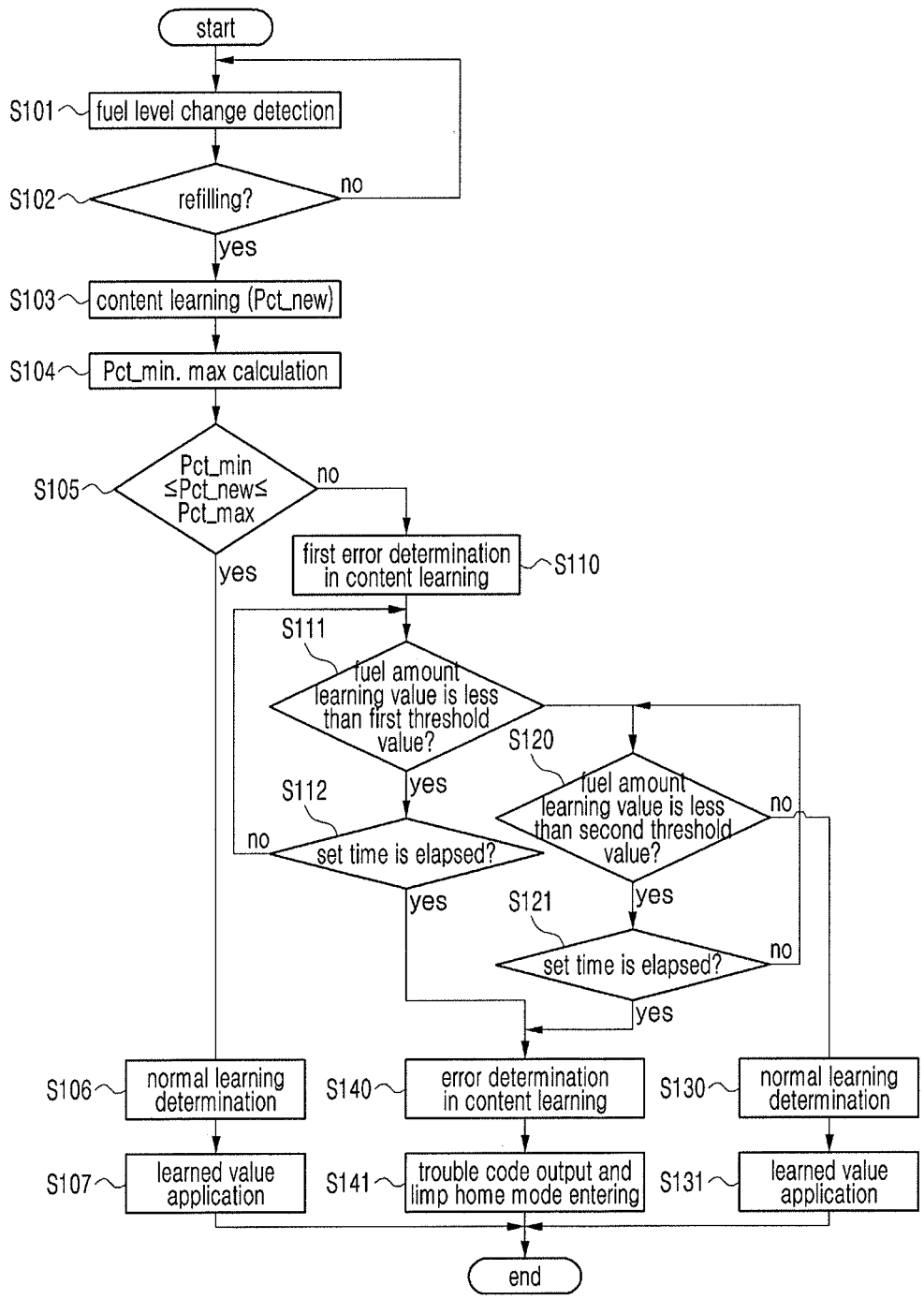
FIG. 1 is a flowchart showing a conventional ethanol content compensation method.
Figure 2:
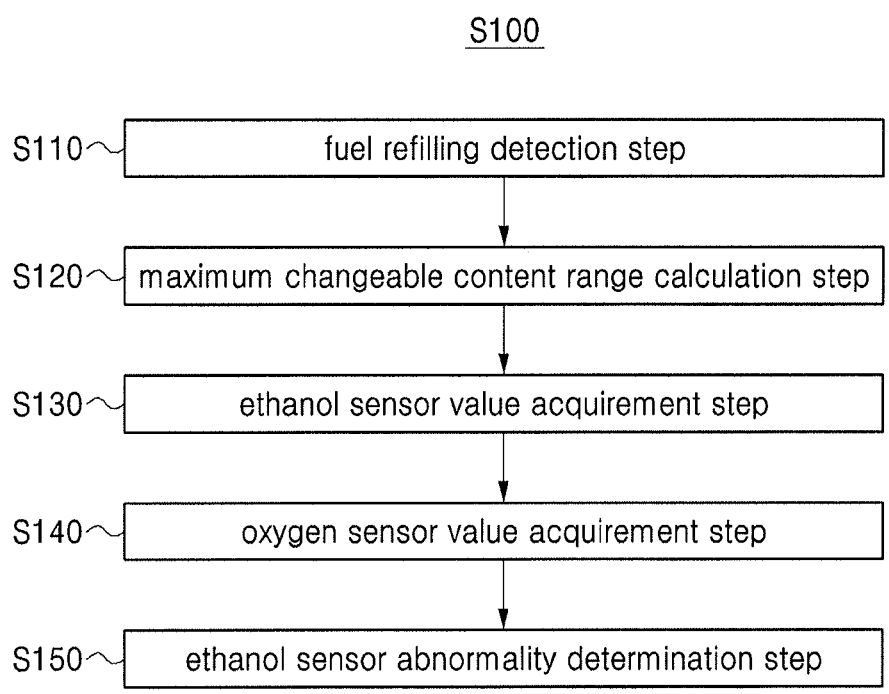
FIG. 2 is a flowchart view showing a diagnosis method for an ethanol sensor of an FFV according to the present invention.
Figure 3:
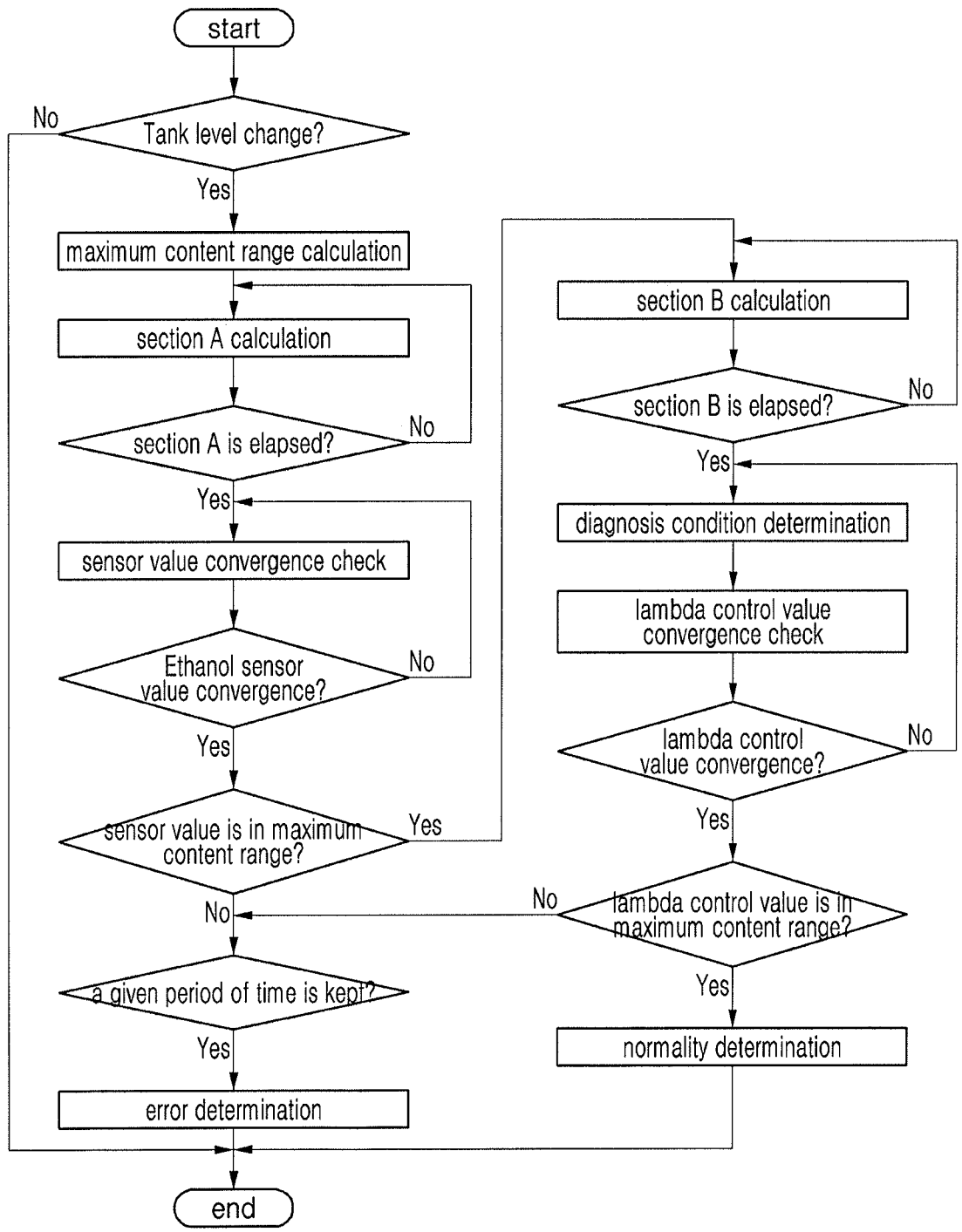
FIG. 3 is a flowchart showing a detailed process of the diagnosis method for an ethanol sensor of an FFV according to the present invention.
Figure 4:
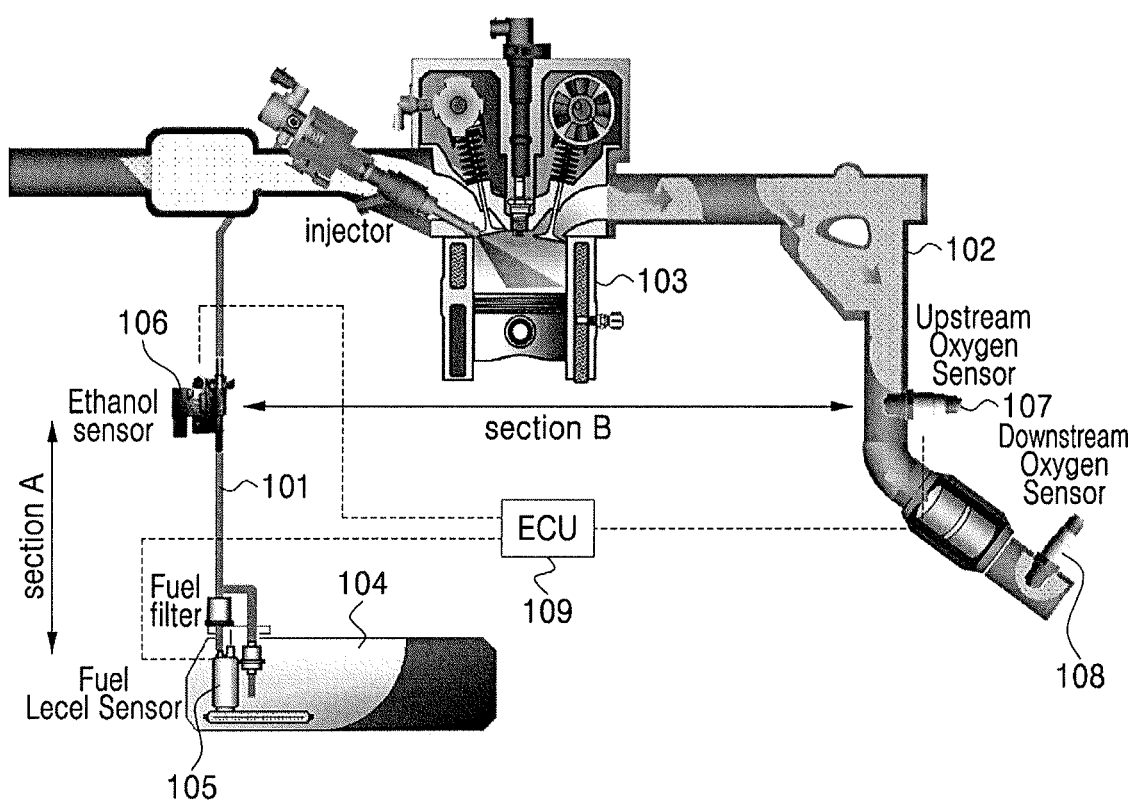
FIG. 4 is a schematic view showing a configuration of an FFV according to the present invention.

FIG. 2 is a flowchart view showing a diagnosis method for an ethanol sensor of an FFV according to the present invention, and FIG. 3 is a flowchart showing a detailed process of the diagnosis method for an ethanol sensor of an FFV according to the present invention. FIG. 4 is a schematic view showing a configuration of an FFV according to the present invention.

As shown, a diagnosis method S100 for an ethanol sensor of an FFV according to the present invention includes a fuel refilling detection step S110, a maximum changeable content range calculation step S120, an ethanol sensor value acquirement step S130, an oxygen sensor value acquirement step S140, and an ethanol sensor abnormality determination step S150.

In detail, the fuel refilling detection step S110 is a step of detecting whether fuel is filled to a fuel tank through a fuel refilling detection device disposed in the fuel tank. At this time, the fuel refilling detection device disposed in the fuel tank is a fuel level sensor, a fuel refilling switch, or a fuel refilling sensor.

The maximum changeable content range calculation step S120 is a step of calculating a content range of ethanol in the fuel stored in the fuel tank on the basis of whether the fuel refilled is pure gasoline or pure ethanol.

In detail, the maximum changeable content range calculation step S120 calculates the content range of ethanol in the fuel stored in the fuel tank on the basis of ethanol content data stored in advance before refilling, volume data of the fuel stored in the fuel tank before refilling, and a volume of fuel refilled.

At this time, a minimum limit value in a changeable content is calculated under the assumption where the fuel refilled is pure gasoline, and a maximum limit value in a changeable content is calculated under the assumption where the fuel refilled is pure ethanol.

As shown in FIGS. 2 and 3, the ethanol sensor value acquirement step S130 is carried out after the maximum changeable content range calculation step S120.

The ethanol sensor value acquirement step S130 is a step of calculating an amount of ethanol remaining on a line between the fuel tank and an ethanol sensor, calculating time during which the fuel refilled reaches the ethanol sensor, and after the calculated time is elapsed, determining whether the data detected from the ethanol sensor converges into a given value.

In detail, the calculated time is acquired by calculating a target value of the fuel remaining between the fuel tank and the ethanol sensor by using length and inner diameter data on the line disposed between the fuel tank and the ethanol sensor, estimating an amount of fuel injected into an interior of an engine, comparing whether the estimated amount of fuel is greater than the target value of the fuel, and calculating the time during which the fuel refilled reaches the ethanol sensor.

Otherwise, the calculated time is acquired by calculating a remaining amount value of fuel between the fuel tank and the ethanol sensor by using length and inner diameter data on the line disposed between the fuel tank and the ethanol sensor, estimating an injection amount value of fuel per hour into an interior of an engine, dividing the remaining amount value of fuel by the injection amount value of fuel per hour, and calculating the time during which the fuel refilled reaches the ethanol sensor.

At this time, as shown in FIG. 3, if the data detected from the ethanol sensor does not converge into the given value after the calculated time is elapsed, desirably, the data is repeatedly detected from the ethanol sensor until it converges into the given value.

The oxygen sensor value acquirement step S140 is a step of calculating an amount of exhaust gas remaining on a line between the engine and an oxygen sensor, calculating time during which the exhaust gas of the fuel refilled reaches the oxygen sensor, and after the calculated time is elapsed, determining whether the data detected from the oxygen sensor converges into a given value.

In detail, the time during which the exhaust gas of the fuel refilled reaches the oxygen sensor is acquired by calculating, if the data detected from the ethanol sensor converges into the given value, arrival time at the oxygen gas from the engine according to load and RPM (resolutions per minutes). At this time, change time of fuel from the ethanol sensor to the engine is desirably calculated.

Otherwise, the time during which the exhaust gas of the fuel refilled reaches the oxygen sensor is acquired by calculating a remaining amount value of exhaust gas between the fuel tank and the ethanol sensor by using length and inner diameter data on the line disposed between the engine and the oxygen sensor, detecting an emission amount value of exhaust gas per hour from the engine, dividing the remaining amount value of exhaust gas by the emission amount value of exhaust gas per hour, and calculating the time during which the exhaust gas emitted by the combustion of the fuel refilled reaches the oxygen sensor from the engine.

At this time, if the data detected from the oxygen sensor does not converge into the given value after the calculated time is elapsed, desirably, the data is repeatedly detected from the oxygen sensor until it converges into the given value.

In some cases, as shown in FIG. 3, if the data detected from the oxygen sensor converges into the given value, a lambda control value convergence determination step S146 is further carried out to determine whether convergence of a deviation or lambda control value from a lambda, 1 of the oxygen sensor is carried out.

At this time, if it is determined that convergence of the lambda control value is carried out at the lambda control value convergence determination step S146, desirably, a diagnosis condition determination step S145 is further carried out to determine whether the current operating conditions of the FFV are under diagnosis conditions.

Desirably, the diagnosis conditions include constant engine RPM and range condition satisfaction, constant engine load and range condition satisfaction, rich/lean control condition of air-fuel ratio, excessive injection control section, canister purge valve closing, an amount of ethanol evaporated below a given level, error of an air flow measuring system (MAP, HFM), error of an injector, and misfire or knocking error.

After the diagnosis condition determination step S145, as shown in FIG. 3, if it determined that convergence of the lambda control value is carried out at the lambda control value convergence determination step S146, a lambda control value allowable range determination step S147 is carried out to determine whether the lambda control value is within a predetermined target lambda control value allowable range.

At this time, if it is determined that the lambda control value is within the predetermined target lambda control value allowable range at the lambda control value allowable range determination step S147, it is determined that the ethanol sensor is normal.

After a series of steps as mentioned above have been carried out, the ethanol sensor abnormality determination step S150 can be carried out.

Figure 5:
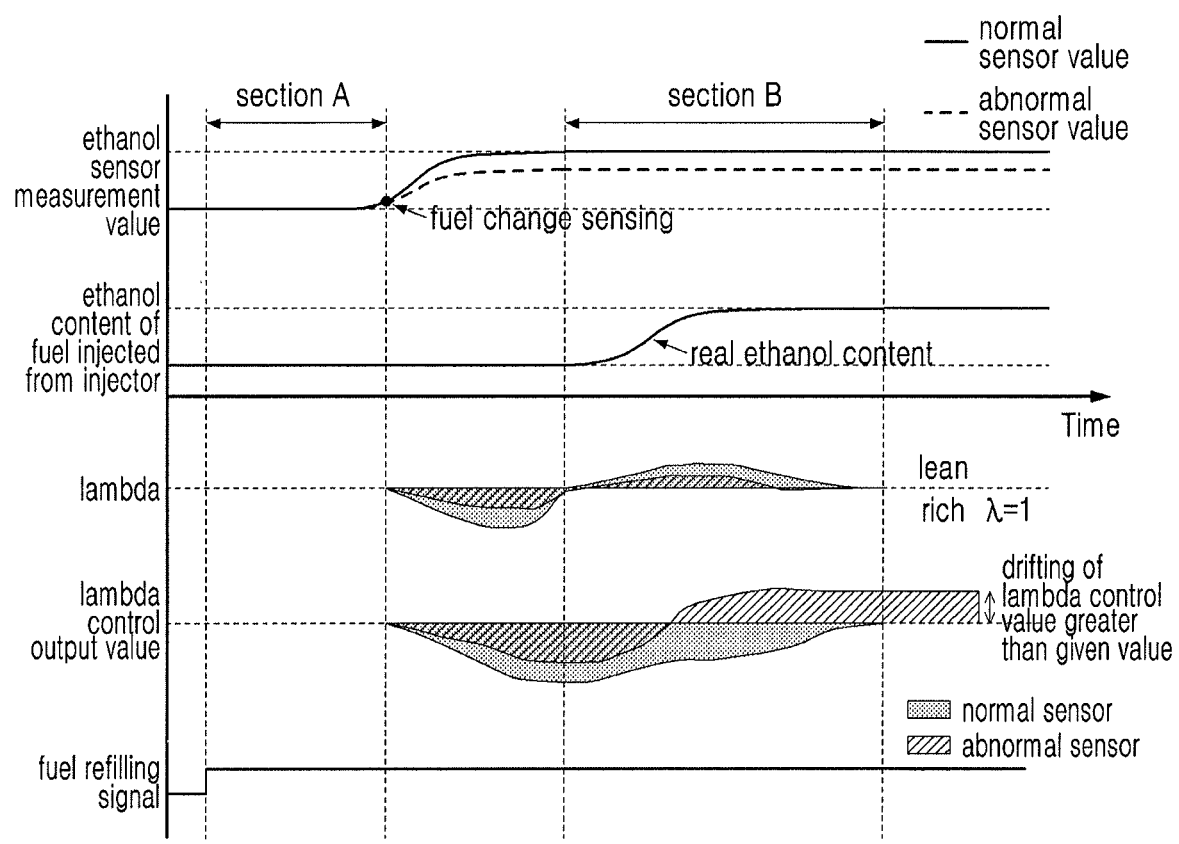
FIG. 5 is a graph showing a case where data values detected from the configuration of the FFV according to the present invention converge or do not converge into specific values as time is elapsed.

In detail, as shown in FIGS. 2, 3 and 5, the ethanol sensor abnormality determination step S150 is a step of determining that an error is generated from the ethanol sensor if the data acquired at the ethanol sensor value acquirement step S130 or the data acquired at the oxygen sensor value acquirement step S140 is not a value in the calculated range.

On the other hand, the present invention relates to an FFV operated by the diagnosis method for the ethanol sensor according to the present invention.

In detail, as shown in FIG. 4, the FFV according to the present invention includes a fuel refilling detection device 105, an ethanol sensor 106, an oxygen sensor 107, and an engine control unit 109.

According to the present invention, the fuel refilling detection device 105 is disposed in a fuel tank 104 to detect whether fuel is filled to the fuel tank 104.

The ethanol sensor 106 is mounted on a fuel supply line 101 between the fuel tank 104 and an engine 103 to detect data on an ethanol content in the fuel supplied from the fuel tank 104 to the engine 103.

The oxygen sensor 107 is mounted on an exhaust gas emission line 102 of the exhaust gas discharged from the engine 103 to detect data on an amount of exhaust gas discharged from the engine 103.

According to the present invention, the engine control unit 109 determines that an error is generated from the ethanol sensor if the data acquired at the ethanol sensor value acquirement step S130 or the data acquired at the oxygen sensor value acquirement step S140 is not a value in the calculated range.

As described above, the diagnosis method for the ethanol sensor of the FFV according to the present invention includes the fuel refilling detection step, the maximum changeable content range calculation step, the ethanol sensor value acquirement step, the oxygen sensor value acquirement step, and the ethanol sensor abnormality determination step, so that abnormity of the ethanol sensor is accurately diagnosed and the ethanol content of the fuel stored in the fuel tank is accurately detected, thereby completely solving the problems occurring when it is recognized that the detected ethanol content is greater or less than the real ethanol content.

In addition, the FFV according to the present invention includes the fuel refilling detection device, the ethanol sensor, the oxygen sensor, and the engine control unit, so that abnormity of the ethanol sensor is accurately diagnosed and the ethanol content of the fuel stored in the fuel tank is accurately detected, thereby completely solving the problems occurring when it is recognized that the detected ethanol content is greater or less than the real ethanol content.

The present invention may be modified in various ways and may have several exemplary embodiments. Specific exemplary embodiments of the present invention are illustrated in the drawings and described in detail in the detailed description. However, this does not limit the invention within specific embodiments and it should be understood that the invention covers all the modifications, equivalents, and replacements within the idea and technical scope of the invention.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A diagnosis method for an ethanol sensor (106) of a flexible fuel vehicle, the flexible fuel vehicle having a fuel refilling detection device (105) disposed in a fuel tank (104), the ethanol sensor (106) disposed on a fuel supply line (101), and an oxygen sensor (107) disposed on an exhaust gas emission line (102), the diagnosis method comprising:
   a) the fuel refilling detection step (S110 of detecting whether fuel is filled to the fuel tank (104) through the fuel refilling detection device (105) disposed in the fuel tank (104);
   b) the maximum changeable content range calculation step (S120) of calculating a content range of ethanol in the fuel stored in the fuel tank (104) on the basis of whether the fuel refilled is pure gasoline or pure ethanol;
   c) the ethanol sensor value acquirement step (S130) of calculating an amount of ethanol remaining on a line between the fuel tank (104) and the ethanol sensor (106), calculating time during which the fuel refilled reaches the ethanol sensor (106), and after the calculated time is elapsed, determining whether the data detected from the ethanol sensor (106) converges into a given value;
   d) the oxygen sensor value acquirement step (S140) of calculating an amount of exhaust gas remaining on a line between an engine (103) and the oxygen sensor (107), calculating time during which the exhaust gas of the fuel refilled reaches the oxygen sensor (107), and after the calculated time is elapsed, determining whether the data detected from the oxygen sensor (107) converges into a given value; and
   e) the ethanol sensor abnormality determination step (S150) of determining that an error is generated from the ethanol sensor (106) if the data acquired at the ethanol sensor value acquirement step (S130) or the data acquired at the oxygen sensor value acquirement step (S140) is not a value in the calculated range.

2. The diagnosis method according to claim 1, wherein the fuel refilling detection device (105) disposed in the fuel tank (104) is a fuel level sensor, a fuel refilling switch, or a fuel refilling sensor.

3. The diagnosis method according to claim 1, wherein the maximum changeable content range calculation step (S120) calculates the content range of ethanol in the fuel stored in the fuel tank (104) on the basis of ethanol content data stored in advance before refilling, volume data of the fuel stored in the fuel tank (104) before refilling, and a volume of fuel refilled.

4. The diagnosis method according to claim 3, wherein the maximum changeable content range calculation step (S120) calculates a minimum limit value in a changeable content under the assumption where the fuel refilled is pure gasoline and calculates a maximum limit value in a changeable content under the assumption where the fuel refilled is pure ethanol.

5. The diagnosis method according to claim 1, wherein the calculated time at the ethanol sensor value acquirement step (S130) is acquired by calculating a target value of the fuel remaining between the fuel tank (104) and the ethanol sensor (106) by using length and inner diameter data on the line disposed between the fuel tank (104) and the ethanol sensor (106), estimating an amount of fuel injected into an interior of the engine (103), comparing whether the estimated amount of fuel is greater than the target value of the fuel, and calculating the time during which the fuel refilled reaches the ethanol sensor (106).

6. The diagnosis method according to claim 1, wherein at the ethanol sensor value acquirement step (S130), if the data detected from the ethanol sensor (106) does not converge into the given value after the calculated time is elapsed, the data is repeatedly detected from the ethanol sensor (106) until the data converges into the given value.

7. The diagnosis method according to claim 1, wherein at the oxygen sensor value acquirement step (S140), the time during which the exhaust gas of the fuel refilled reaches the oxygen sensor (107) is acquired by calculating time during which the exhaust gas of the fuel reaches the oxygen gas (107) from the engine (103) according to operating ranges, if the data detected from the ethanol sensor (106) converges into the given value, and by calculating change time of fuel from the ethanol sensor (106) to the engine (103).

8. The diagnosis method according to claim 7, wherein at the oxygen sensor value acquirement step (S140), the time during which the exhaust gas of the fuel refilled reaches the oxygen sensor (107) is acquired by calculating a remaining amount value of exhaust gas between the fuel tank (104) and the ethanol sensor (106) by using length and inner diameter data on the line disposed between the engine (103) and the oxygen sensor (107), detecting an emission amount value of exhaust gas per hour from the engine (103), dividing the remaining amount value of exhaust gas by the emission amount value of exhaust gas per hour, and calculating the time during which the exhaust gas emitted by the combustion of the fuel refilled reaches the oxygen sensor (107) from the engine (103).

9. The diagnosis method according to claim 1, further comprising the diagnosis condition determination step (S145) of determining whether current operating conditions of the FFV are under diagnosis conditions after the calculated time is elapsed.

10. The diagnosis method according to claim 1, wherein at the oxygen sensor value acquirement step (S140), if the data detected from the oxygen sensor (107) does not converge into the given value after the calculated time is elapsed, the data is repeatedly detected from the oxygen sensor (107) until the data converges into the given value.

11. The diagnosis method according to claim 1, further comprising the lambda control value convergence determination step (S146) of determining whether convergence of a deviation or lambda control value from a lambda, 1 of the oxygen sensor is carried out if the data detected from the oxygen sensor (107) converges into the given value.

12. The diagnosis method according to claim 11, further comprising the lambda control value allowable range determination step (S147) of determining whether the lambda control value is within a predetermined target lambda control value allowable range if it determined that convergence of the lambda control value is carried out at the lambda control value convergence determination step (S146).

13. The diagnosis method according to claim 12, wherein if it is determined that the lambda control value is within the predetermined target lambda control value allowable range at the lambda control value allowable range determination step (S147), it is determined that the ethanol sensor (106) is normal.

14. The diagnosis method according to claim 9, wherein the diagnosis conditions comprise constant engine RPM and range condition satisfaction, constant engine load and range condition satisfaction, rich/lean control condition of air-fuel ratio, excessive injection control section, canister purge valve closing, an amount of ethanol evaporated below a given level, error of an air flow measuring system (MAP, HFM), error of an injector, and misfire or knocking error.

15. A flexible fuel vehicle operated by the diagnosis method for the ethanol sensor according to claim 1, the flexible fuel vehicle comprising:
the fuel refilling detection device (105) disposed in the fuel tank (104) to detect whether the fuel is filled to the fuel tank (104);
the ethanol sensor (106) mounted on the fuel supply line (101) between the fuel tank (104) and the engine (103) to detect data on an ethanol content in the fuel supplied from the fuel tank (104) to the engine (103);
the oxygen sensor (107) mounted on the exhaust gas emission line (102) of the exhaust gas discharged from the engine (103) to detect data on an amount of exhaust gas discharged from the engine (103); and
an engine control unit (109) for determining that an error is generated from the ethanol sensor (106) if the data acquired at the ethanol sensor value acquirement step (S130) or the data acquired at the oxygen sensor value acquirement step (S140) is not a value in the calculated range.

* * * * *